United States Patent [19]

Leong

[11] Patent Number: 5,354,555
[45] Date of Patent: Oct. 11, 1994

[54] VACCINE TO CONTROL THE VIRAL INFECTION OF FISH

[75] Inventor: Jo-Ann C. Leong, Albany, Oreg.

[73] Assignee: State of Oregon Acting By and Through The State Board of Higher Education on Behalf of Oregon State University, Eugene, Oreg.

[21] Appl. No.: 27,742

[22] Filed: Mar. 8, 1993

Related U.S. Application Data

[63] Continuation of Ser. No. 239,775, Sep. 2, 1988, abandoned, which is a continuation-in-part of Ser. No. 722,130, Apr. 10, 1985, abandoned.

[51] Int. Cl.$^5$ .................. A61K 39/12; C12P 21/06
[52] U.S. Cl. .................. 424/186.1; 435/69.1; 435/69.3; 424/224.1; 424/817
[58] Field of Search ............. 424/89; 435/69.1, 69.3

[56] References Cited

U.S. PATENT DOCUMENTS 4,333,922 6/1982 Herschler ..................... 424/89

FOREIGN PATENT DOCUMENTS 0177657 9/1984 European Pat. Off.

OTHER PUBLICATIONS

Kurath and Leong, "Characterization of Infectious Hematopoietic Necrosis Virus mRNA Species Reveals a Nonvirion Rhabdovirus Protein," *J. Virol.* 53:462–468, 1985.

Kurath et al., "Molecular cloning of the Six mRNA Species of Infectious Hematopoietic Necrosis Virus, a Fish Rhabdovirus, and Gene Order Determination by R-Loop Mapping," *J. Virol.* 53:469–476, 1985.

Hsu and Leong, "A Comparison of Detection Methods for Infectious Haematopoietic Necrosis Virus," *J. Fish. Dis.* 8:1–12, 1985.

Leong et al., "Strains of Infectious Hematopoietic Necrosis (IHN) Virus may be Identified by Structural Protein Differences," *Int. Symp. Fish Biologics: Serodiagnostics and Vaccines*, Leetown, W.V., USA, 1981. *Devel. Biol. Std.* 49:43–55, Karger, 1981.

Koener et al., "Nucleotide Sequence of a cDNA Clone Carrying the Glycoprotein Gene of Infectious Hematopoietic Necros Virus, a Fish Rhabdovirus," *J. Virol.* 61:1342–1349, 1987.

Kurath and Leong, "Transcription in Vitro of Infectious Haematopoietic Necrosis Virus, a Fish Rhabdovirus," *J. Gen. Virol.* 68:1767–1771, 1987.

Gilmore et al., "Expression in *Escherichia coli* of an Epitope of the Glycoprotein of Infectious Hematopoietic Necrosis Virus Protects Against Viral Challenge," *Bio/Tech.* 6:295–300, 1988.

Kurath, G., "Molecular Characterization of Infectious Hematopoietic Necrosis Virus Transcription and Genome Organization," Ph.D Thesis, Oregon State University, Corvallis, Oreg., 1984.

Hill et al., "Physico-chemical and Serological Characterization of Five Rhabdoviruses Infecting Fish," *J. Gen. Viro.* 27:369–378, 1975.

Yelverton et al., "Rabies Virus Glycoprotein Analogs: Biosynthesis in *Escherichia coli*," *Science* 219:614–620, 1983.

Kieny et al., "Expression of Rabies Virus Glycoprotein from a Recombinant Vaccinia Virus," *Nature* 312:163–166, 1984.

(List continued on next page.)

*Primary Examiner*—Christine M. Nucker
*Assistant Examiner*—Lynette F. Smith
*Attorney, Agent, or Firm*—Klarquist Sparkman Campbell Leigh & Whinston

[57] ABSTRACT

Subunit vaccines and their use for immunizing fish against infection by viruses are disclosed. In particular, plasmid pG8 is constructed by joining, with the plasmid pUC8, DNA which encodes the glycoprotein of infectious hematopoietic necrosis virus (IHNV). *E. coli* cells are transformed by pG8, whereby pure viral antigen is produced to provide a vaccine for the control of IHNV in fish.

6 Claims, 5 Drawing Sheets

OTHER PUBLICATIONS

McAllister and Wagner, "Virion RNA Polymerases of Two Salmonid Rhabdoviruses," *J. Virol.* 22:839–843, 1977.

Malek et al., "The Rabies Glycoprotein Gene is Expressed in *Escherichia coli* as a Denatured Polypeptide," in *Modern Approaches to Vaccines,* Cold Spring Harbor Laboratory, New York 1984.

Wunner et al., "Rabies Subunit Vaccines," *J. Gen. Virol.* 64:1649–1656, 1983.

Vieira and Messing, "The pUC Plasmids, an M13mp7–derived System for Insertion Mutagenesis and Sequencing with Synthetic Universal Primers," *Gene* 19:259–268, 1982.

Pasquier, "Antibody Diversity in Lower Vertebrates–Why Is It So Restricted?", *Nature* 296:311—313 (1982).

A B C D E F G H

FIG. 6
FIG. 7
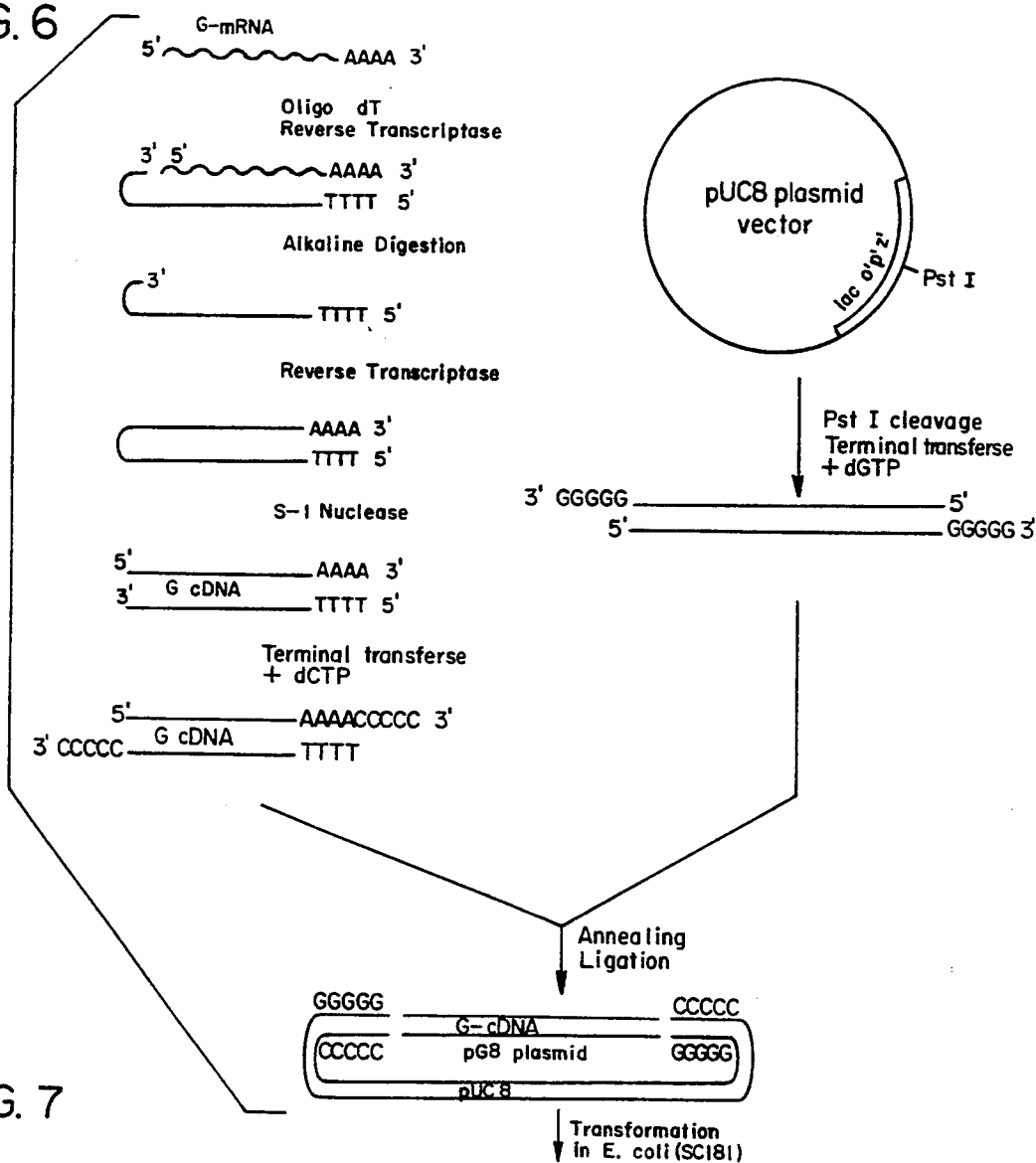
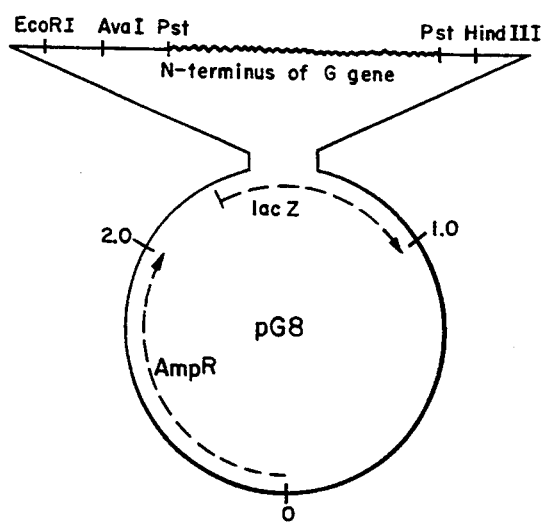

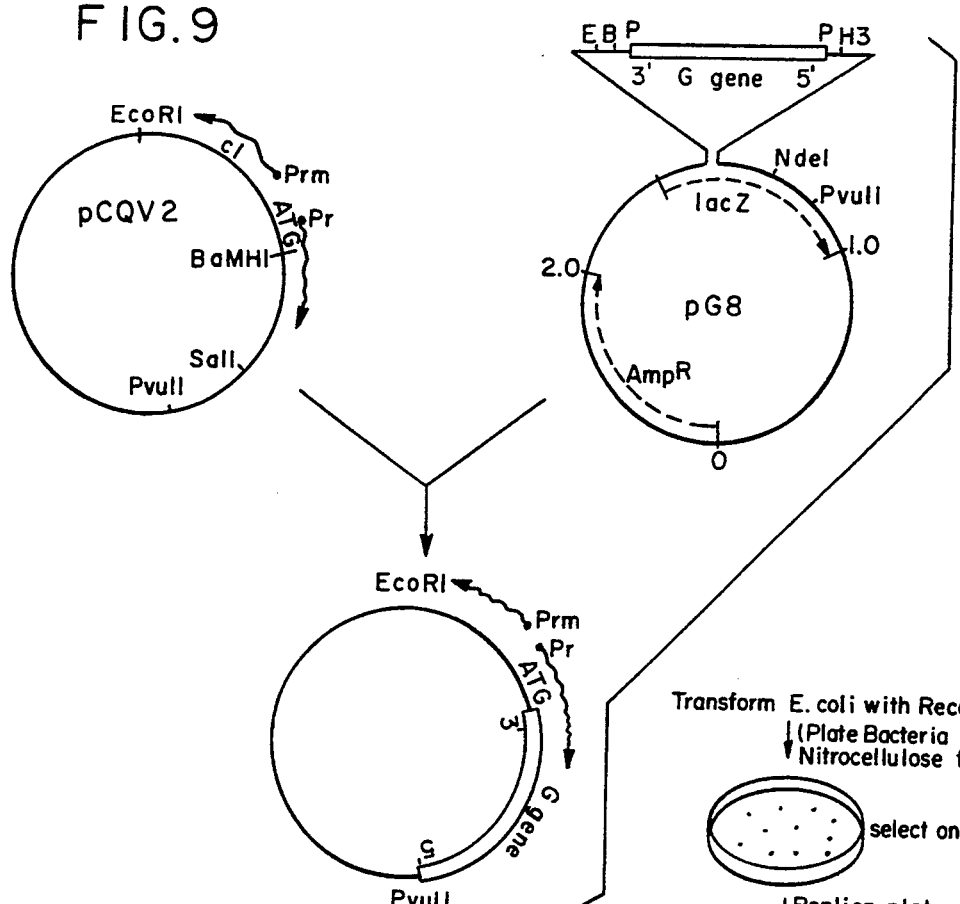

VACCINE TO CONTROL THE VIRAL INFECTION OF FISH

This invention was made with government support under Grant No. 901-15-139, awarded by the U.S. Department of Agriculture, Science and Education Administration and under Agreement No. DE-A179-84BP16479, Project 84-43, awarded by the U.S. Department of Energy, Bonneville Power Administration. The government has certain rights in this invention.

CROSS REFERENCE TO RELATED APPLICATION

This application is a continuation of United States patent application Ser. No. 07/239,775, filed on Sep. 2, 1988, now abandoned, which was a continuation-in-part of United States patent application Ser. No. 06/722,130, filed Apr. 10, 1985, now abandoned.

BACKGROUND OF THE INVENTION

1. Field of the Invention

This invention relates to the control of viral infections of fish, and more specifically to vaccines for such control.

2. General Discussion of the Background

Viral diseases of fish are increasing throughout the world, threatening the future of both ocean and freshwater fisheries. The problem of infection is particularly acute among fry in hatcheries where populations are dense and diseases are rapidly transmitted.

For example, in recent years, an alarming increase in the incidence of infectious hematopoietic necrosis (IHN) virus in fish has been observed at trout and salmon hatcheries. Since its initial isolation in 1953, IHN virus has spread throughout the Pacific Coast of Northern America. It is now found in 60- to 90-percent of spawning sockeye salmon in Alaska.

Efforts to control the spread of IHN virus in the Columbia River Basin alone resulted in the destruction of more than 14 million eggs and fish in 1980-82. The magnitude of the losses were such that fish production quotas could not be met at certain hatcheries. Thus, IHN disease is costly and threatens the continued existence of valuable fisheries.

IHN virus most severely affects fry and juvenile salmon or trout. The infected fish generally appear normal until shortly before death when they become darker and show hemorrhages at the bases of fins and at the throat. The kidneys and spleen are the most severely affected organs.

An epizootic of IHN is characterized by an abrupt and high mortality among the infected population. In fish up to two months of age, the mortality can exceed 90 percent. Fish from two to six months of age have a mortality rate of 50 percent and in 6- to 12-month-old fish, the mortality rate is 10 percent. The disease has not been seen in fish two years of age or older.

The actual route of IHN virus transmission in nature is unknown. However, experimental studies have shown that the virus can be transmitted through water from infected fish as well as by ingestion of diseased fish carcasses. Congenital transmission of the virus from adult carrier fish to their young is thought to be the principal mode of transmission. The virus is frequently found in the ovarian or seminal fluid of carrier fish at the time of spawning. Thus, IHN virus is believed to be transmitted on eggs as an external contaminant.

Presently, the only practical method available to control the spread of IHN virus is the removal and destruction of all infected fish, the disinfection of all ponds and equipment, and the restocking of the hatchery with virus-free eggs. Since IHN virus is believed to be transmitted with eggs as an external contaminant, eggs are disinfected with iodophore treatment for 10 minutes at pH 6.0. The effectiveness of this treatment is still controversial since eggs are water-hardened before the iodophore bath. The water hardening process may allow virus to enter the egg and thus make the virus insensitive to iodophore treatment.

Another method of disease control is the rearing of susceptible fish at water temperatures above 15° C. This method is not usually feasible on a large scale since 15° C. water temperatures are difficult to easily and economically obtain.

Killed virus vaccines and live, attenuated virus vaccines have been used as prophylactic measures in man for years. However, both types of vaccine give rise to undesirable side effects. In both preparations, there are nonviral proteins, e.g. cellular material, that may induce undesirable auto-allergic antibodies.

Furthermore, extensive work must be done to insure the safety of live, attenuated viral vaccines. Before such vaccines may be released for widespread use, 1) the degree and stability of attenuation must be established by extensive laboratory and clinical trials; 2) the attenuated virus strain should exhibit low communicability under field use; 3) reliable "marker" tests must be developed to allow differentiation of virulent and attenuated virus strains; 4) the vaccine preparation must be free from other viral contaminants; 5) the attenuated virus strain must also be nononcogenic; and 6) the attenuated virus must not establish persistent infections with consequent chronic disease in the host. These requirements usually make the mass production of a live, attenuated virus vaccine too costly for animal species other than humans.

Despite the low likelihood of developing a practical vaccine, both killed and live modified types of IHNV (IHN virus) vaccines have been tested experimentally (Rohevec, et al., *Natl. Sci. Council Symp.*, Series No. 3, Natl. Sci. Council, Taipei, Taiwan, pp. 115-121, 1981), because none of the other available treatments is very successful.

An attenuated strain of IHN virus was developed in 1974 (McMichael, Ph.D. Diss., Oregon State University, 1974). The vaccine was produced by transferring an Oregon sockeye salmon isolate on steelhead trout cells in tissue culture for more than forty passages. The attenuated virus immunizes sockeye salmon fry or juveniles after contact with the virus for 48 hours. In most trials, 90 percent or more of the vaccinated fish were protected against a fatal infection with the wild-type virus for as long as 110 days (Tebbit, Ph.D. Diss., Oregon State University, 1976; Fryer, et al., *CRC Crit. Rev. Micro.*, 7:287–344, 1976). Attenuated strains are not, however, in commercial use since they are virulent in rainbow trout and the reversion frequency from nonpathogenic to pathogenic wild-type virus has not been determined.

Amend and Smith, *J. Fish. Res. Bd. Can.*, 31:1371–1378, 1974, showed that rainbow trout will develop neutralizing antibody within 54 days after injection with killed virus. Sera obtained from these fish were protective when juvenile fish were passively immunized and experimentally challenged with virulent virus.

Although the experimental tests of Amend and Smith have shown that a killed IHN viral vaccine is effective, the cost and labor-intensive procedures required for preparing a killed viral vaccine make it impractical for widespread use at fish hatcheries.

Thus, no practical vaccine, antiviral chemical, or passive immunization therapy has heretofore been available to eliminate or ameliorate a viral disease in fish.

A recently developed method for producing viral vaccines is the biosynthesis of a viral subunit component. In this method, the gene for the viral protein is isolated and provided with new regulatory signals appropriate for its expression in a new host organism. For example, the gene for the major surface antigen of hepatitis B virus has been directly expressed both in the yeast *Saccharomyces cerevisiae* (Valenzuela, et al., *Nature*, 298:347–350, 1982) and in simian cells (Liu and Levinson, in *Eucaryotic Viral Vectors* (V. Gluzman, ed.), Cold Spring Harbor Laboratory, Cold Spring Harbor, New York, 1982). Similarly, vaccines have been developed to resist human diseases caused by herpes 1 and 2 viruses and polio-virus.

Kleid and coworkers have reported the synthesis in *Escherichia coli* of an immunogenic fusion protein between an antigen, VP3, of foot-and-mouth disease virus and a protein derived from the *E. coli* pathway for tryptophan biosynthesis (Kleid, et al., *Science*, 214:1125–1129, 1981).

One possible method for producing a virus-subunit vaccine is to use a known nucleotide sequence to deduce the amino acid sequence of an immunogenic viral protein. Then, short polypeptides are selected from the deduced sequence and chemically synthesized, attached to carrier proteins of known immunogenicity, and injected in an immunopotentiating adjuvant. As illustrated for the cases of hepatitis virus and foot-and-mouth disease virus (Lerner, et al., *Proc. Natl. Acad. Sci. USA*, 78:3403–3407, 1981; Bittle, et al., *Nature*, 298:30–33, 1982; Sutcliffe, et al., *Science*, 219:660–666, 1983), in some instances, a given linear array of amino acids can be an effective antigenic domain; the native three-dimensional structure of the intact protein is not required to evoke a spectrum of reactive and neutralizing antibodies in vivo.

One area of recent activity on viral subunits has been with the rabies virus which, like IHNV, is also a bullet-shaped, enveloped rhabdovirus (Hill, et al., *J. Gen. Virol.*, 27:369–378, 1975). Although both rabies and IHN viruses produce G proteins, the viruses do not immunologically cross-react (Hill, et al., supra), indicating that G proteins from the two viruses are appreciably different.

The full-length coding sequence of one strain of rabies G mRNA has been determined and its sequence or portions thereof expressed in a bacterial host (Yelverton, et al., *Science*, 219:614–620, 1983; Goeddel and Yelverton, European Patent No. 0117657, 1984). However, no protection against rabies infection using the bacterially synthesized material has yet been reported (Kieny, et al., *Nature*, 312:163–166, 1984). Kieny, et al. (supra), constructed a recombinant vaccinia virus (VV) whose genome contained the rabies glycoprotein cDNA. Inoculation of rabbits and mice with live recombinant VV induced production of anti-rabies antibodies and protection against subsequent challenge with live rabies virus. These results suggest that some required rabies G-protein post-translational processing occurs in eucaryotic cells, but not bacterial cells. For rabies virus, this is a serious limitation on large-scale vaccine production because culturing sufficient numbers of eucaryotic cells on their required solid supports is difficult and labor-intensive. Bacterial culture in suspension, on the other hand, would be much simpler to perform on a virtually unlimited large scale.

IHNV is different from other rhabdoviruses in other respects. First, essentially no homology exists between mRNAs from IHNV and viral hemorrhagic septicemia (VHS) virus, another salmonid rhabdovirus (McAllister and Wagner, *J. Virol.*, 22:839–843, 1977). Second, the IHNV viral genome is unique in encoding six, rather than the five, viral proteins normally associated with rhabdoviruses (Kurath and Leong, *J. Virol.*, 53:462–468, 1985). Hence, an effective process for producing an anti-IHNV vaccine comprised of immunogenic IHNV G protein or portions thereof, suitable for administering to fish on a large scale at low cost, and that contains no live or attenuated viruses of any sort, cannot be extrapolated from work performed with other viruses, even those within the same taxonomic group.

Thus, despite advances with other viruses, until the present invention, there has been no successful attempt to create a subunit vaccine suitable for practical administration to large numbers of fish.

SUMMARY OF THE INVENTION

It has now been discovered that fish can be vaccinated simultaneously in large numbers against IHNV infections by the use of viral subunit vaccines comprising the entire IHNV antigen polypeptide or portions thereof. Such vaccines can be mass-produced by the culturing of bacterial cells that contain expression vectors (recombinant plasmids) comprising DNA encoding for the viral antigen or immunogenic portions thereof. The plasmids are capable of expressing the viral antigen in the bacteria when cultured under appropriate conditions. After a defined culture period, the cells are disrupted and suspended in a solution appropriate to serve as a fish vaccine.

By such molecular cloning methods, it is possible to provide an inexpensive, subunit vaccine for fish that has none of the drawbacks of live viral vaccines. The problems of recombination and reversion to virulence are eliminated. Moreover, with efficient expression of the virus protein in bacteria, vaccine production becomes very inexpensive in contrast to the production costs projected for a killed virus vaccine.

Specifically, subunit vaccine to IHNV has now been developed by recombinant DNA techniques. The viral genes encoding the viral glycoprotein (G protein) responsible for inducing a protective immune response in fish has been isolated and sequenced and a sequence deduced for the corresponding polypeptide. The gene has been cloned and recombined with bacterial control elements in a plasmid to allow its efficient expression in a bacterial host. Large quantities of IHNV G protein may now be synthesized in bacteria and used to immunize fish against IHNV infection. The result is a safe, inexpensive vaccine for fish against IHN virus.

Accordingly, an object of the present invention is to provide safe, effective, and economical viral vaccines to control viral infections of fish, particularly infections of Infectious Hematopoietic Necrosis Virus (IHNV).

Another object is to provide vaccines that cannot revert to a virulent state.

A further object is to provide vaccines that will cause very young fish to develop long term protective immunity.

In particular, it is an object to provide such a vaccine that is effective in interrupting the vertical transmission of viral diseases by immunizing broodstock fish.

An additional object is to provide vaccines that are economical to manufacture and effective against multiple strains of a fish-disease virus.

And, yet another object is to provide a vaccine that will be effective to immunize multiple species of fish.

A particular object is to provide a vaccine to immunize salmonid species against IHNV.

These and other objects and features of the invention will be apparent from the following description and accompanying drawings.

BRIEF DESCRIPTION OF THE DRAWINGS

In the drawings:

FIG. 6 is a schematic diagram of steps in the construction of the pG8 plasmid containing the IHNV glycoprotein gene;

FIG. 7 is a genetic map of plasmid pG8 showing the orientation of the glycoprotein gene;

FIG. 9 diagrams the construction of a recombinant plasmid containing the trpE promoter and gene fused to a fragment of the IHNV G gene;

FIG. 10 shows the strategy used to sequence the IHNV G gene cloned in pG8; and

FIG. 11 shows the nucleotide sequence of the IHNV G gene, showing the predicted glycoprotein amino acid sequence and the codon usage.

DETAILED DESCRIPTION

Subunit fish vaccines against IHNV (a fish disease virus) are produced by first cleaving DNA complementary to the viral RNA genome using appropriate restriction endonucleases. By hybridization analyses, specific fragments of the cleaved cDNA that encode for the viral G protein or a portion thereof are identified. Recombinant expression vectors containing DNA encoding for all or a portion of the IHNV G protein are then made by cleaving an appropriate expression vector capable of replicating in a bacterial host, and mixing the resulting cut vector DNA with specific fragments of cleaved viral cDNA. After the polypeptide product is released from the bacterial host cells, it can be added to water containing young fish who become immune thereby to subsequent infection by the virus.

I. The IHN Virus

Infectious hematopoietic necrosis virus (IHNV) is a bullet-shaped virus which belongs to the Lyssavirus group of rhabdoviruses. It is similar to rabies virus in the arrangement of its virion proteins. The virion is large, 90×160 nm (600 S), with a lipid-containing envelope. The viral genome is single-stranded RNA of ca. 10,900 bases, with a sedimentation velocity of 40–45 S in sucrose and a molecular weight of $3.8 \times 10^6$ daltons in glyoxal agarose gels.

Figure 1:
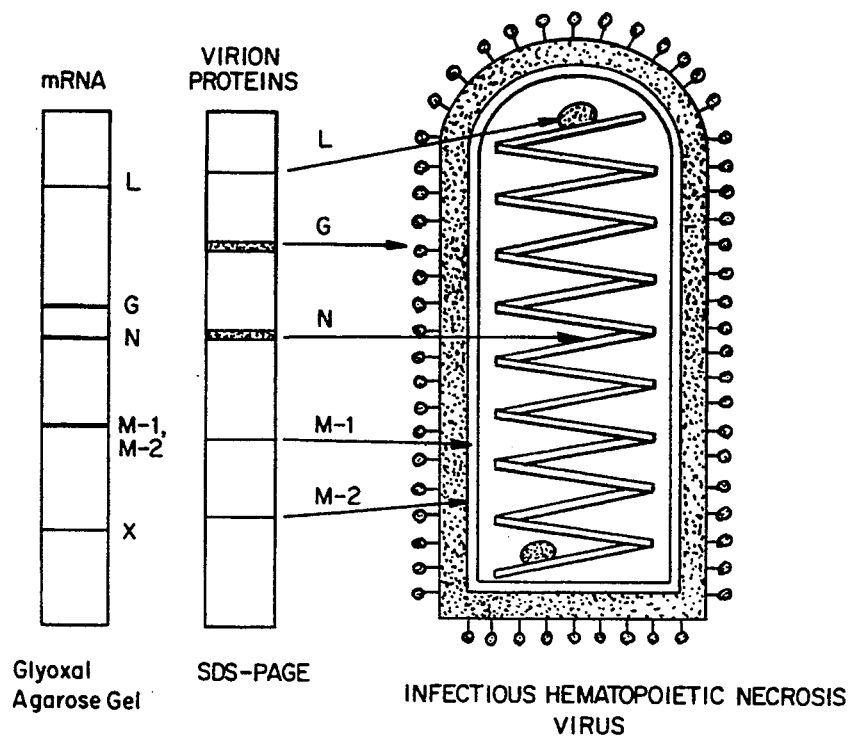
FIG. 1 is a diagrammatic representation of the IHN virion denoting molecular weights in kilodaltons (Kd) of the virion proteins of IHNV. Arrows point to the presumed locations of the virion proteins in the virus.
Figure 8:
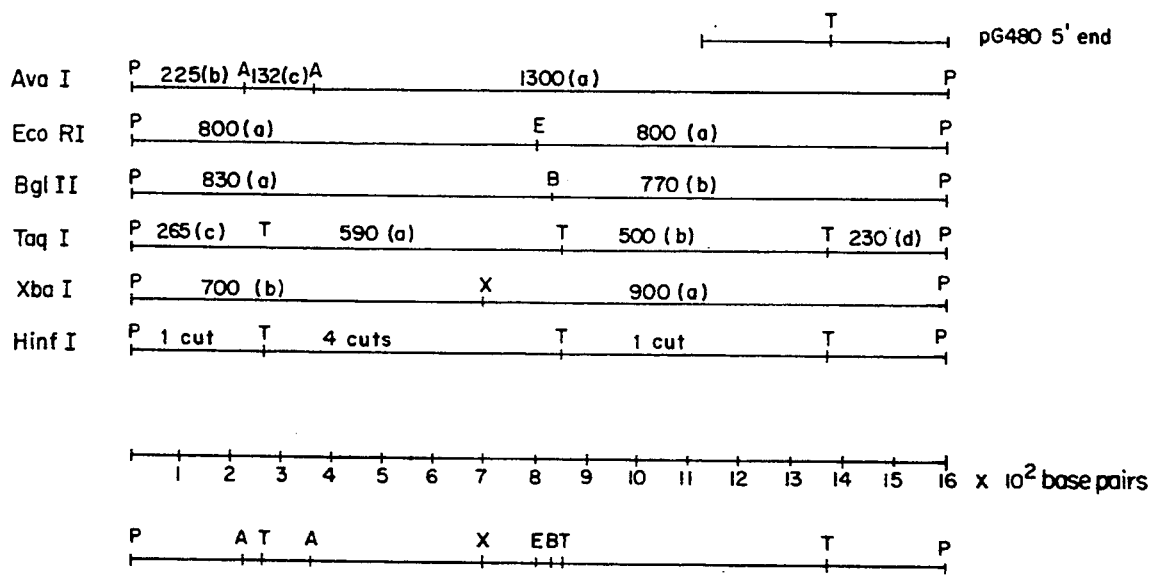
FIG. 8 is a restriction map of the cloned IHNV glycoprotein gene.

It has been known for some time that five viral polypeptides can be found in the virion. These polypeptides have average molecular weights of 150,000 (L protein=polymerase), 70,000 (G protein=glycoprotein), 42,000 (N protein=nucleoprotein), 22,000 (M-1 protein =matrix protein), and 17,000 (M-2 protein=matrix protein) (McAllister and Wagner, *J. Virol.*, 22:839443, 1977; Leong, et al., *International Symposium on Fish Biologics: Sero-Diagnostics and Vaccines. Developments in Biological Standardization*, 49:43–55, 1981). The N and M-2 proteins are phosphoproteins. FIG. 1 is a schematic diagram of the virus particle and the five proteins.

Although IHNV resembles the mammalian rhabdovirus prototypes, vesicular stomatitis virus, and rabies, there are some significant differences. In particular, it has now been discovered that the IHNV genome also encodes a nonvirion protein, designated the NV protein, as described in Kurath and Leong, *J. Virol.*, 53:462–468, 1985, which is incorporated herein by reference. The NV protein is induced in infected cells but is not present in mature virions.

The entire virus replication cycle takes place in the cytoplasm of infected fish cells. Chinook salmon cells (CHSE-214) will produce new virus within four hours after infection at 18° C. There is an increased synthesis of virus until 20 hours postinfection. At least two types of virus particles are produced. At low multiplicities of infection (MOI), the majority of new virions are complete, infectious particles ("B" particles). At high multiplicities of infection (MOI greater than 10 plague-forming-units (PFU)/cell), incomplete, noninfectious particles (truncated, or "T" particles) are produced, which interfere with the replication of whole virus.

The virus is extremely stable in water at 10° C. The infectivity of IHNV in water is almost unchanged after 2.5 weeks. Increased salinity lowers the stability of the virus. In Hanks buffered salt solution, the virus is almost completely inactivated in five days at 10° C. This salt effect is eliminated by the addition of 10-percent calf serum or EDTA to 0.01M.

The virion contains an RNA-dependent RNA polymers which will catalyze the synthesis of viral nRNA in a test tube (McAllister and Wagner, *J. Virol.*, 22:839–843, 1977). The optimal conditions for the synthesis of the mRNA in vitro in the presence of S-adenosylmethionine and HEPES buffer are described in Kurath and Leong, *J. Virol.*, 53:462–468, 1985. The mRNA species for each of the viral proteins have been identified by hybrid selection as described in Kurath, et al., *J. Virol.*, 53:469–476, 1985, which is incorporated herein by reference.

II. The Glycoprotein of IHNV Induces Protective Immunity

A. Isolation and Purification of IHNV Glycoprotein

The first step in creating a subunit vaccine was to isolate subunit IHNV glycoprotein (G protein) material which could act as an antigen.

In the past, a comparison of specific monocomponent antiserum against the structural polypeptides of VSV or rabies virus has shown that the antibody to the G protein confers immunity (Dietzschold, et al., *J. Virol.*, 14:1–7, 1974; Wiktor, et al., *J. Immunol.*, 110:269–276, 1973).

Accordingly, the glycoprotein or G protein of IHNV was isolated from a purified Round Butte strain virus obtained from two liters of supernatant fluid from infected cells by detergent lysis and batch elution through SM-2 biobeads (Bio-Rad). The IHNV glycoprotein was released from purified virions with a nonionic detergent, Triton X-100. Since a concentration of detergent was used that differentially solubilized the glycoprotein from the rest of the virion proteins, it was possible to purify the glycoprotein by centrifugation.

In a first such procedure for obtaining purified glycoprotein, chinook salmon embryo cells (CHSE-214) were grown as monolayers in Eagle's minimum essential medium (MEM) supplemented with 10-percent heat inactivated fetal bovine serum. These cells were infected with IHNV from a reference stock which had been plaque-purified. Virus for experimental purposes was prepared by infecting the cell monolayers with a multiplicity of infection (MOI) of 1–10 PFU/cell and incubated at 18° C. At 4–7 days postinfection, the virus was harvested from the growth medium. Yields of 50–500 PFU/cell or $5 \times 10^7$ PFU/mL were normally obtained in this virus-cell system.

The virus was concentrated by ultracentrifugation through 50-percent glycerol in STE buffer (0.1M NaCl; 0.02M Tris-hydrochloride, pH 7.5; 0.01M EDTA). The virus pellet was resuspended in STE buffer, sonicated, layered onto an 11-mL gradient of 10- to 40-percent sucrose (w/v in STE buffer) and centrifuged in a Beckman SW41 rotor for 45 minutes at 32,000 rpm. The virus band for complete "B" particles was further purified by banding in a gradient of 5- to 30-percent sucrose in STE in the SW41 rotor for 0.5 hours at 36,000 rpm.

The initial identification of the IHNV G protein was made with radioactively labeled virus. At 6–10 hours postinfection, the virus were labeled with $^3$H-6-D-glucosamine, 10–30 $\mu$Ci/mL in MEM with 1/100 the normal glucose concentration and supplemented with 2X nonessential amino acids and 2-percent dialyzed fetal calf serum. At 24 hours postinfection, this labeling medium was diluted 2-fold with normal growth medium and incubation was continued.

To obtain purified viral glycoprotein, purified virions were suspended in 10 mM Tris-hydrochloride buffer (pH 7.4) at a protein concentration of 1 mg/mL, treated with 2-percent (v/v) Triton X-100 at 25° C. for 60 minutes at room temperature. In the absence of salt, only the G protein of IHN virus is solubilized by Triton X-100 (McAllister and Wagner, *J. Virol.*, 15:733–738, 1975).

The initial virus protein concentration was 1 mg/mL in a total volume of 1 mL. The solubilized glycoprotein was then separated from the particulate, insoluble protein by centrifugation at 140,000$\times$g for 1 hour in a Beckman SW50.1 rotor. The G protein remained in the supernatant fluid. Analysis by polyacrylamide gel electrophoresis of the sample indicated that the G protein preparation was pure and that the concentration of the protein was 0.04 mg/mL in 5.0 mL.

The Triton X-100 was removed by batch elution of the preparation through a column of Bio Beads SM-2 (Bio-Rad). The procedure was repeated four more times. Less than 0.01-percent Triton-X-100 remained as measured by absorbance at 275 nm. No observable loss of G protein occurred and a single G protein bang was observed after polyacrylamide gel electrophoresis and staining with silver nitrate.

Figure 4:
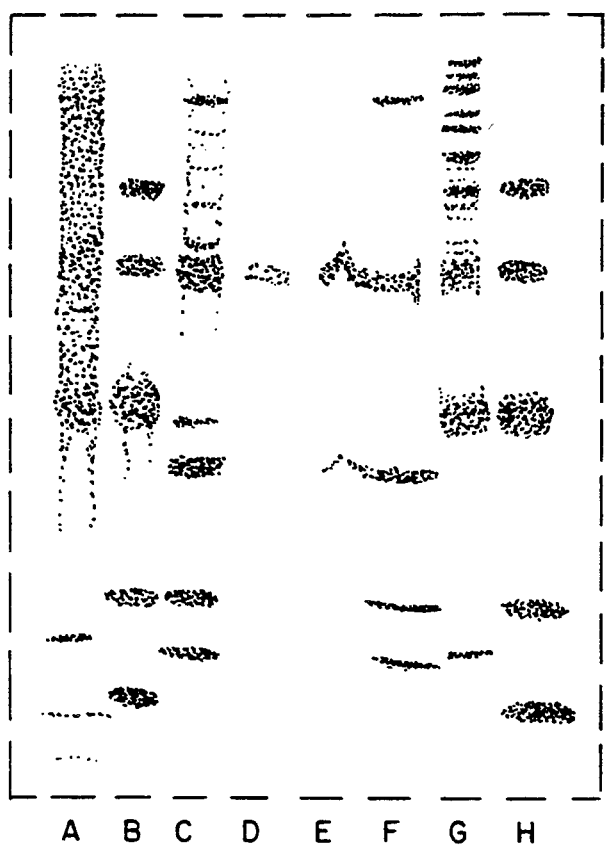
FIG. 4 is a photograph of a silver-stained slab gel of IHNV glycoproteins purified from IHN virions.

In a second such procedure for obtaining purified glycoprotein, fifty 150 cm$^2$ flasks, each containing culture medium and a monolayer of CHSE-214 cells, were infected with IHNV (0.01 MOI). Infected cells were harvested from supernatant fluid at seven days postinfection. The virus was then purified by serial velocity and isopycnic centrifugation, and the virus protein concentration determined by the Biorad Protein assay (usual concentration is 1 $\mu$g/$\mu$L). The virus were lysed by contact for one hour at 20° C. with 1-percent Triton X-100, 0.01M Tris-hydrochloride, at pH 7.6. The lysate was centrifuged in a SW50.1 rotor at 45,000 rpm for one hour at 4° C. to obtain a protein concentration of about 45 ng/$\mu$L. The resulting G protein supernatant fluid was then stored at $-70°$ C. (usual volume is 5 mL, usual recovery is 50 percent of the virion G protein). The purity of G protein was assessed by polyacrylamide gel electrophoresis and silver staining of the gel, as shown in FIG. 4. Detergent removal was accomplished by five batch-elutions of the G protein-containing fluid through SM-2 Biobead columns. Afterward, the Triton X-100 concentration was less than 0.01 percent. Recovery was 90 percent of the G protein at 36 ng/$\mu$L.

B. Immunogenicity Testing of Purified G Protein With Fish

To determine whether fish are immunoreactive to IHNV glycoprotein antigen, fish weighing 0.5 g were immunized by intraperitoneal injection or immersion as follows: fish anesthetized with benzocaine were injected with 10 $\mu$L of a solution containing approximately 0.5 $\mu$g of purified G protein. Immersion was performed in a plastic beaker containing 4 mL of a solution of purified G protein (40–50 $\mu$g/mL) in 0.01M Tris-hydrochloride buffer pH 7.6. One hundred fish were immersed in the solution for 1–2 minutes and then released into a holding tank containing running water at 12° C.

After one month, the immunized and mock-immunized fish were divided into 4 groups of 25 fish each and challenged for 18 hours with live IHNV at $10^{-2}$, $10^{-3}$, $10^{-4}$, or $10^{-5}$ dilutions of the stock virus in one-liter holding tanks. These dilutions represented approximately $2 \times 10^6$, $2 \times 10^5$, $2 \times 10^4$, and $2 \times 10^3$ TCID$_{50}$ doses per mL of water. After challenge, the fish were returned to the normal tanks and examined daily. Any dead fish found each day were transported on ice to the laboratory, weighed, and processed for IHN virus isolation.

C. Isolation of IHNV From Infected Fish

Dead fish were processed immediately for virus isolation. The fish were weighed and diluted (w/v) 1:10 with Hanks Buffered Salt Solution, and then macerated in a stomacher processor (Tekmar). The resulting suspension was clarified by centrifugation and the supernatant solution was treated (1:5 dilution) with antibiotics, Penicillin/Streptomycin (1,000 units/mL, 1,000 $\mu$g/mL), Fungazone (500 IU/mL), and Gentamicin (0.25/mL) in PBS overnight at 4° C. The next day, the fluid was inoculated directly onto CHSE-214 cells and EPC cells in multi-well plates (Engelking and Leong, *Virol.*, 109:47–58, 1978). The cells were observed daily for cytopathic effects for two weeks.

Figure 2:
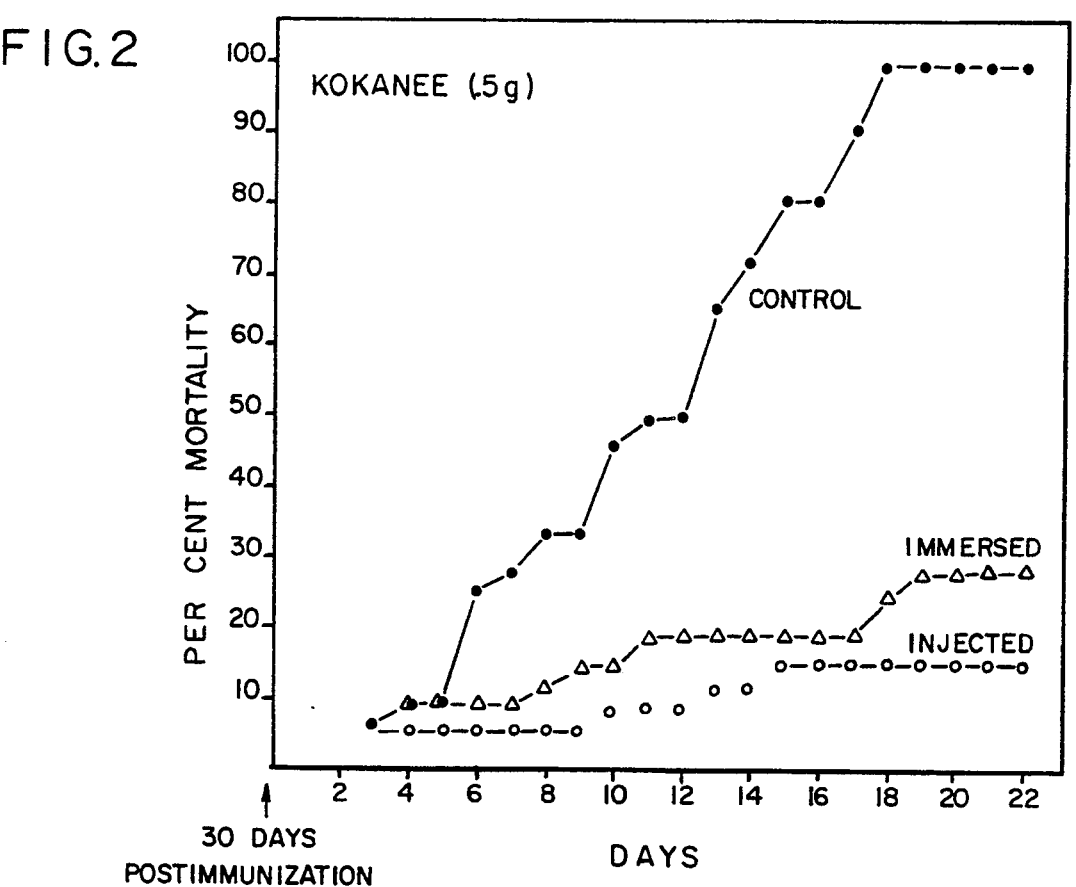
FIGS. 2 and 3 are graphs showing the extent to which salmonid fry are immunized by IHNV glycoprotein.
Figure 3:
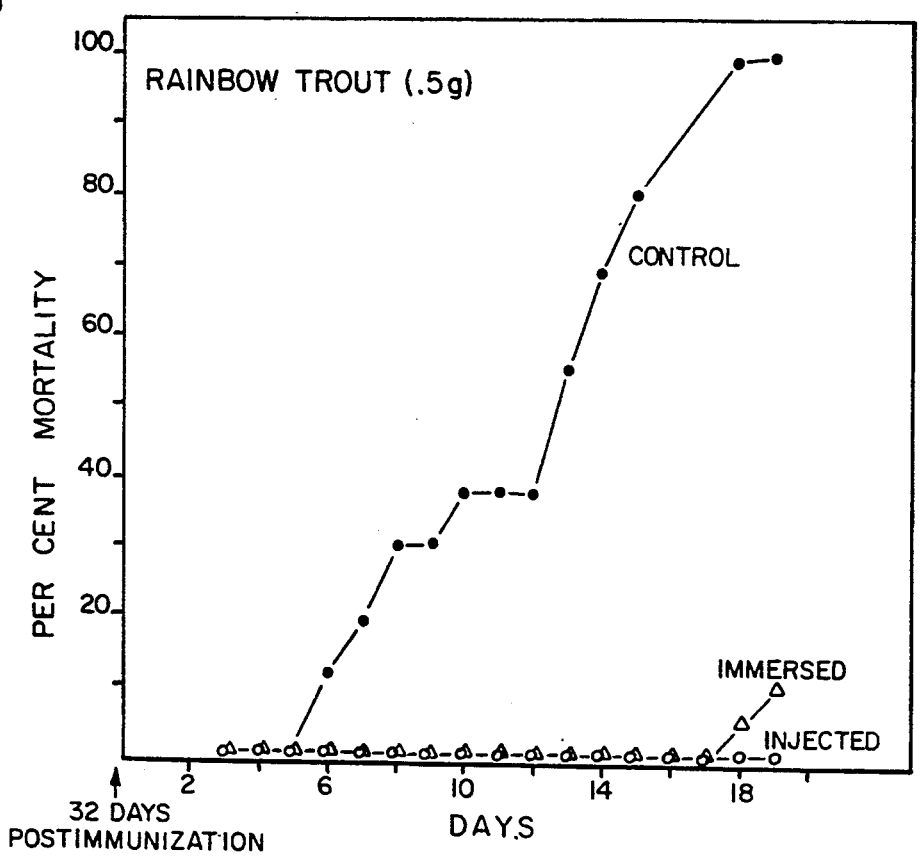

The results of one test with Kokanee salmon fry are shown in FIG. 2. It is apparent that the immunized fish were protected from the virus challenge. Even more dramatic is the immunization data obtained with rainbow trout fry shown in FIG. 3. In this study, both immersed and injected fish were equally protected from live virus challenge. Thus, it was determined that a G-protein vaccine induces protective immunity to IHNV.

II. Construction Isolation, and Characterization of Bacterial Plasmids Containing IHNV Viral Genes Although IHNV can be obtained by tissue culture, the relatively low yield from infected eucaryotic cells makes it preferable to produce the desired genetic material by cloning. Accordingly, cDNA clones, carrying sequences from each of the six mRNA species of the IHN viral genome, have been constructed.

Each of the resulting six species of transcribed DNA was subsequently inserted into the plasmid vector, pUC8, as described in Kurath, et al., *J. Virol.*, 53:469–476, 1985.

A. Cloning of Viral mRNA Species

In particular, polyadenylated RNA was isolated from IHNV-infected chinook salmon (CHSE-214) cells as described in Kurath and Leong, *J. Virol.*, 53:462–468, 1985. For use as a cloning template, this RNA was passed twice over an oligodeoxythymidylic acid-cellulose column to remove all detectable host cell ribosomal RNA. The preparation of double-stranded cDNA was carried out by the procedure of Land, et al., *Nucl. Acids Res.*, 9:2251–2267, 1981. This procedure includes 4 mM sodium pyrophosphate in the first-strand cDNA reaction to prevent the formation of the terminal hairpin loop and eliminate the need for S1 nuclease digestion.

Briefly, 20 μg of polyadenylated RNA were reverse transcribed to synthesize 3.9 μg of single-stranded cDNA in a reaction containing the RNA template, an oligo(dT)$_{(12-18)}$ primer, placental RNase inhibitor (Enzo Biochemicals, Inc.), and reverse transcriptase (Life Science Div., The Mogul Corp.). Tails of ca. 20 dCMP residues were added to this single-stranded cDNA with terminal deoxynucleotidyl transferase, and these molecules were rendered double-stranded in a second reverse transcriptase reaction containing oligo(dG)$_{(12-18)}$ (Collaborative Research, Inc.) as the primer. Nicks or gaps in these double-stranded molecules were filled by incubation with Klenow enzyme (Maniatis, et al., *Molecular Cloning*, Cold Spring Harbor Laboratory, Cold Spring Harbor, N.Y., 1982), and the products of this reaction were tailed with dCMP residues.

The plasmid vector, pUC8, was cleaved with the restriction S endonuclease PstI (Bethesda Research Laboratories), and deoxyguanylic acid tails of ca. 15 residues were added. The deoxyguanylic acid-tailed vector and deoxycytidylic acid-tailed cDNA were annealed at a molar ratio of 1:1. This DNA was used to transform two host strains of *Escherichia coli* K-12:JM103 (see: Messing, et al., *Nucl. Acids Res.*, 9:309–321, 1981), and C600 SC181 (see: Appleyard, *Genetics*, 39:440–452, 1954).

Transformation was carried out with freshly prepared competent cells by the calcium chloride shock method (Mandel and Higa, *J. Mol. Biol.*, 53:159–162, 1970). Transformants were plated on LB agar (Maniatis, et al., *Molecular Cloning*, Cold Spring Harbor Laboratory, Cold Spring Harbor, N.Y., 1982) containing 150 μg/mL ampicillin. The transformation efficiencies were 51 and 158 ampicillin-resistant transformants per ng of reannealed DNA for JM103 and SC181, respectively. The control transformation efficiency was $5 \times 10^3$ transformants per ng of uncleaved pUC8 for both strains.

B. Preparation of cDNA Probe

The probe for viral-specific sequences was $^{32}$P-labeled DNA complementary to the IHNV genome RNA. Probe synthesis was carried out at 42° C. for 105 minutes in a 50-μL reaction containing 1 μg of fragmented viral genome RNA; 0.5 μg of calf thymus random primer fragments; 50 mM Tris-hydrochloride (pH 8.3); 40 nM MgCl$_2$; 0.4 mM dithiothreitol; 0.2 mM dATP, 0.2 mM dGTP, 0.2 mM dTTP, and 0.01 mM [$^{32}$P]dCTP (specific activity, 800 Ci/mmol; New England Nuclear Corp.); and 40 U of reverse transcriptase (Life Science Div.). After synthesis the reaction was adjusted to 0.6N NaOH and incubated at 37° C. for 30 minutes. The reaction was then neutralized by adding HCl to 0.6N and Tris-hydrochloride (pH 8.1) to 200 mM. This mixture was passed over a 5-mL column of Sephadex G-50, and fractions containing incorporated radioactivity were pooled, adjusted to 0.3M potassium acetate, and precipitated with 2.5 volumes of ethanol. This probe typically had a specific activity of $2 \times 10^7$ cpm/μg.

C. Colony Blots

Transformants were screened for viral sequences by the procedure of Taub and Thompson, (*Anal. Biochem.*, 126:222–230, 1982), in which fresh colonies were replicated onto sterile Whatman 541 filter paper and washed successively in NaOH, lysozyme, proteinase I, and phenol-chloroform-isoamyl alcohol (25:41:1). Filters were hybridized with $2 \times 10^6$ to $5 \times 10^6$ cpm of $^{32}$P-labeled cDNA probe.

D. Isolation of Plasmid DNA

Small-scale plasmid preparations (1 to 2 μg) were made by a modification of the alkaline lysis procedure (Birnboim and Doly, *Nucl. Acids Res.*, 7:1513–1523, 1979). Fresh colonies of each transformant were scraped from plates with a toothpick and dispersed in 40 μL of a lysing buffer composed of 0.5-percent sodium dodecyl sulfate, 50 mM NaOH, 5 mM EDTA, and 2-percent Ficoll. These mixtures were incubated for 30 minutes at 68° C. Sucrose and bromphenol blue were added to 5 and 0.002 percent, respectively, and the samples were loaded onto a horizontal 0.7-percent agarose gel in Tris-acetate buffer (0.72M Tris-hydrochloride, 0.1 mM acetate, 20 mM EDTA, pH 7.9). After electrophoresis for 12 to 16 h at 25 V, the gel was stained with ethidium bromide and examined with a UV transilluminator (Fotodyne, Inc.).

Large-scale isolation of plasmid DNA was carried out by the boiling method of Holmes and Quigley, (*Anal. Biochem.*, 114:193–197, 1981).

E. Determination of Cloned Viral Sequence Size

The restriction endonuclease PstI (Bethesda Research Laboratories) was used to cleave 300 ng of each purified plasmid. The released cloned insert DNA was separated from the plasmid vector DNA by electrophoresis on a vertical 7.5-percent acrylamide gel with a 3.75-percent acrylamide stacking gel. The Laemmli gel system (Laemmli, *Nature*, 227:680–685, 1970) was used with the exception that sodium dodecyl sulfate was omitted from all buffers. Electrophoresis was carried out at 30 mA through the stacking gel and 50 mA through the lower gel. After electrophoresis, the gel was stained with ethidium bromide, and photographs of the UV-illuminated gel were made with Polaroid type 47 film. The sizes of the cloned inserts were determined by comparison with HinfI and HaeIII pBR322 restriction fragment size standards. The cloned plasmid specific for the glycoprotein gene had an insert size of 440 base pairs.

F. Preparation of Nick-Translated Probes

Nick translation of cloned plasmids was carried out in 10-μL reactions containing 200 ng of plasmid DNA (Maniatis, et al., *Molecular Cloning*, Cold Spring Harbor Laboratory, Cold Spring Harbor, N.Y., 1982 and Rigby, et al., *J. Mol. Biol.*, 113:237–251, 1977). Nick-translated probes had a specific activity of $2 \times 10^7$ to $5 \times 10^7$ cpm/μg.

G. DNA Blot Hybridizations

Cloned plasmids were cleaved with the restriction endonuclease PstI (Bethesda Research Laboratories), and the cloned inserts were separated from vector DNA by electrophoresis on 0.7-percent agarose gels in Tris-acetate buffer. The DNA was alkaline-denatured, transferred to a nitrocellulose membrane by the Southern blot method (Maniatis, et al., *Molecular Cloning*, Cold Spring Harbor Laboratory, Cold Spring Harbor, N.Y., 1982 and Southern, *J. Mol. Biol.*, 98:503–517, 1975), and baked onto the filter for 2 h at 80° C. in vacuo. Hybridization of the blots was as described by Maniatis, et al. (supra), with the exception that both prehybridization and hybridization were carried out in 50-percent formamide at 42° C. Each hybridization included $2 \times 10^6$ to $10 \times 10^6$ cpm of $^{32}$P-labeled cDNA probe or nick-translated probe. After hybridization, blots were washed as described by Maniatis, et al. (supra) and exposed to Kodak X-Omat AR X-ray film with a Cronex Lightening-Plus intensifying screen (DuPont Co.) at −70° C.

A high degree of homology between the sequences of two or more different DNA molecules can also be tested for by determining whether the DNA molecules in question, not necessarily cleaved by restriction endonucleases, hybridize to each other under stringent conditions, such as those set forth in Bethesda Research Laboratories, *DNA Detection System Instruction Manual* (Catalog No. 8239SA), pp 8–9 (1984); see also Leary, et al., *Proc. Natl Acad. Sci. USA*, 80:4045–4049, 1983, modifying the procedures of Wahl, et al., *Proc. Natl. Acad. Sci. USA*, 76:3683–3687, 1979.

H. mRNA Blot Hybridization

Characterization of the cloned plasmids required the identification of the specific viral mRNA species which were complementary to each cDNA insert. This was accomplished by probing nitrocellulose blots of the mRNA electrophoretic pattern with $^{32}$P-labeled probes made by nick translation of each of the purified plasmids. The hybridization of $^{32}$P-labeled, nick-translated probes to blots of viral mRNA were carried out by the procedures of Thomas, *Methods Enzymol.*, 100:255–266, 1983. Polyadenylated RNA from IHNV-infected cells was resolved into five bands by glyoxal gel electrophoresis (Kurath, et al., *J. Virol.*, 53:469–476, 1985, and McMaster and Carmichael, *Proc. Natl. Acad. Sci. USA*, 74:4835–4838, 977) and transferred to a nitrocellulose membrane (Thomas, *Methods Enzymol.*, 100:255–266, 1983). The blot was baked for 2 h in vacuo at 80° C. and cut into strips, each containing one gel lane with 2 μg of RNA. The strips were boiled for 5 minutes in 20 nM Tris-hydrochloride (pH 8.0) to remove the glyoxal adducts and hybridized individually with $5 \times 10^6$ to $1 \times 10^7$ cpm of $^{32}$P-nick-translated probes. After hybridization, blots were washed (Thomas, supra) and exposed to X-ray film as described above.

Figure 5:
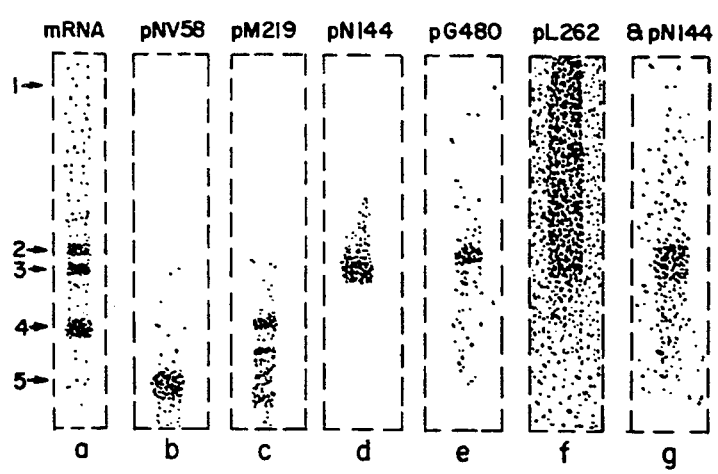
FIG. 5 is a photograph of an autoradiogram of hybridization blots of various plasmids having DNA joined thereto encoding the IHNV protein material.

Examples of plasmids which hybridized specifically to each of the five mRNA bands are shown in FIG. 5.

Identification of the single mRNA band which hybridized with each plasmid DNA probe was made by comparison of the blot autoradiogram with a marker lane of all five mRNA bands (FIG. 5a). However, the proximity of mRNA bands 2 and 3 made it difficult to distinguish hybridization to mRNA band 2 with certainty. Therefore, a double hybridization was carried out with two probes together, pG480 and pN144 (FIG. 5g). The presence of two bands of hybridization confirmed that cDNA clones with sequences from both mRNA bands 2 and 3 had been isolated. Of the 21 plasmids tested, two hybridized to mRNA 1, one hybridized to mRNA 2, eight hybridized to mRNA 3, seven hybridized to mRNA 4, and three hybridized to mRNA 5.

Thus, in particular, the mRNA species for the G protein was isolated after glyoxal agarose gel electrophoresis and identified by in vitro translation of the mRNA species in a rabbit reticulocyte system. The glycoprotein mRNA was then reverse-transcribed into DNA with avian myeloblastosis reverse transcriptase. The DNA was given oligo dC tails using terminal transferase and dCTP. The tailed DNA copy of the viral gene was then inserted into tile PstI cleavage site of the plasmid vector, pUCB, which contains the transcriptional and translational start sequences of the lac Z gene upstream of the PstI site, as shown in FIG. 7. This cleavage site, which is in the lac Z gene fragment of this vector, yielded a fusion protein consisting of the lac Z (beta-galactosidase) protein and the G protein of IHNV.

III. Mapping of Genes on the IHNV Viral Genome by R-Loop Mapping

The cDNA clones of the six mRNA species were used in R-loop analyses to determine the physical order of the genes on the viral genome. The results of this work are described in Kurath, et al., *J. Virol.*, 53:469–476, 1985.

IHNV genomic RNA for R-loop mapping was prepared as described previously (Kurath and Leong, *J. Virol.*, 53:462–468, 1985). Cloned IHNV cDNA plasmids were prepared for large-scale isolation and linearized by cleavage with NdeI (Bethesda Research Laboratories). Formamide (Bethesda Research Laboratories) was deionized by treatment with AG 501-X8 mixed bed ion-exchange resin (Bio-Rad Laboratories). R-loops were formed as described by Chow and Broker, "Mapping RNA:DNA Heteroduplexes by Electron Microscopy," in *Electron Microscopy in Biology, Vol.* 1, p. 139–188, John Wiley and Sons, Inc., New York, 1981, with the following modifications: Linearized plasmid DNA (100 ng) in 18 $\mu$L of 78-percent formamide, 5 mM EDTA was denatured at 80° C. for 10 minutes. IHNV RNA (100 ng) was added to the denatured DNA, the solution was adjusted to 20 $\mu$L of 70-percent formamide, 300 mM NaCl, 4.5 mM EDTA, and R-loops were formed by incubation at 50° C. for 12 to 16 h. Samples (4 $\mu$L each) of the R-loop reaction mixture were spread by the urea-formamide method (Moore, "The Electron Microscopy of Ribonucleic Acids," in *Electron Microscopy in Biology*, Vol. 1, p. 67-88, John Wiley and Sons, Inc., New York, 1981). The hyperphase (40 μL) consisted of 4M urea, 80-percent formamide, 5 mM EDTA, and cytochrome c at a concentration of 40 μg/mL. The hypophase (20 mL) was 50-percent formamide. The DNA-protein film was adsorbed to a Parlodion-coated grid, stained with uranyl acetate, and rotary-shadowed with platinum-palladium. Grids were examined with a Zeiss EM-10A electron microscope operating at 40 kV. Molecular lengths were measured by a calculator-driven digitizer on photographic prints enlarged to a final magnification of 136,000. DNA molecules of known sequence were used as length standards. Double-stranded DNA and RNA-DNA hybrid duplexes had identical contour lengths under the spreading conditions used in these experiments. IHNV RNA lengths were converted to nucleotides, using a unit length of 10,900 nucleotides and correcting for RNA in RNA-DNA hybrid duplexes.

Using these techniques, it was possible to determine that the order of the genes from the N-ward to the L-ward ends of the genome is 3'-N-M1-M2-G-NV-L-5'.

IV. The Construction and Transformation of Plasmid pG8

A new plasmid, containing the complete glycoprotein gene, was constructed to obtain the efficient expression of pure viral antigen. This plasmid was formed by cleaving pUC8 with PstI to allow the insertion of deoxycytidylic acid-tailed cDNA which was found to encode the entire glycoprotein. This process is diagrammed in FIG. 6.

The new plasmid formed by the insertion of the G protein gene into pUC8 has been designated pG8. The orientation of the G protein gene in pG8 has been determined and is shown in FIG. 7, as determined by restriction-fragment overlap analysis.

Plasmid pG8 was transformed into *E. coli* SC181 by growing the host cells in nutrient (L) broth containing ampicillin (60 μg/mL) to an $OD_{550}$ of 0.3. The resulting cells were transferred to centrifuge tubes chilled by ice, and incubated there for 20–30 minutes. The cells were then pelleted by centrifugation for 5 minutes at 6,000 rpm at 4° C. (3000 mx in Sorvall for plastic). After centrifugation, the cells were resuspended in one-half volume of iced 0.1M $CaCl_2$ and stored on ice for 15–20 minutes. The cells were then pelleted by the same procedure and thereafter resuspended in one-fifteenth volume of iced 0.1M $CaCl_2$. The cells were then incubated overnight, on ice, in a 4° C. refrigerator.

The annealed DNA preparation, 50 ng pG8 in TNE annealing buffer, was then added to the cells at a ratio of 50 ng DNA per 200 mL cell suspension. The resulting transformation mixture was held on ice for 30 minutes, then heat-shocked at 37° C. for 90 seconds, and then held on ice for 5 minutes. Next, 1.25 mL of nutrient (L) broth (dilute mix 1:5) was added and the resulting mixture held for 50 minutes at 37° C. without shaking.

The cells were then plated directly onto boiled, sterile nitrocellulose filters (Millipore) overlaying nutrient agar plates (100 μg/mL), DAP (100 μg/mL), and thymine (40 μg/mL). The plates were incubated for 24 hours at 37° C. to obtain the desired transformants.

Replicas of the filters were made by a procedure described by Villa-Komaroff, et al., *Proc. Natl. Acad. Sci. USA,* 75:3727–3731, 1978. The nitrocellulose filters containing the transformants were removed from the agar and placed on a layer of sterile Whatman filter paper. A new sterile filter was placed on top of the filter containing the colonies and pressure was applied with a sterile velvet cloth and replica block. The second filter was placed on a new agar plate and incubated at 37° C. for 48 hours. The colonies on the first filter were screened for the G-specific DNA by in situ hybridization (Grunstein and Hogness, *Proc. Natl. Acad. Sci. USA,* 72:3961–3965, 1975). Positive colonies were rescreened for G-protein synthesis by solid phase radioimmunoassay (Broome and Gilbert, *Proc. Natl. Acad. Sci. USA,* 75:2746–2749, 1978). The reference set produced by replica-plating of the colonies was stored at 2°–4° C.

Detection of colonies containing G-cDNA inserts by in situ hybridization was performed as described by Chang, et al., *Nature,* 275:617–624, 1978. The filter containing the transformed bacterial clones was transferred to a Whatman no. 3 pad saturated with 0.5N NaOH. After 7 minutes, the filter was sequentially transferred to a series of similar pads saturated with 1M Tris-hydrochloride, pH 7.4 (twice, 7 minutes each); 1.5M NaCl, 0.5 M Tris-hydrochloride, pH 7.5 (once, 7 minutes); and 0.3M NaCl, 0.03M Na citrate (2×SSC) (once, 7 minutes). The excess liquid was removed by suction, the filter was placed on a pad containing 90-percent ethanol, dried by suction and baked in vacuo at 80° C. for 2 hours. Before hybridization, filters were treated for 3–6 hours at 65° C. in hybridization buffer that contained 5×SSC, pH 6.1, 0.2-percent SDS, 0.02-percent Ficoll 400 (Pharmacia) and 8 μg/mL *E. coli* tRNA.

Hybridizations were carried out with individual filters in hybridization buffer containing radioactively labeled G-cDNA probe at 65° C. for 24 hours. The filters were then washed in hybridization buffer (once, 60 minutes at 65° C.); in 5×SSC, pH 6.1 (three times, 60 minutes each at 65° C.); and in 2×SSC, pH 7.4 (twice, 10 minutes at room temperature) and air dried. Autoradiograms were obtained by exposing Kodak NS2T No-Screen X-ray film to the filter. Positive colonies were further analyzed for G-protein synthesis.

*E. coli* SC181, containing the transformed plasmid pGB, was deposited at the American Type Culture Collection on Apr. 10, 1985, the deposit having accession number ATCC 53019. The insert is 1590 base pairs long and contains the entire coding sequence for the IHNV glycoprotein gene. A restriction map of the cloned IHNV glycoprotein gene appears in FIG. 8.

V. Determination of IHNV G Gene Nucleotide Sequences

A. Preparation of Clones

A cDNA clone containing the entire coding sequence of the IHNV glycoprotein mRNA (pEg) was used for sequence analysis, as reported in Koener, et al., *J. Virol.,* 61:1342–1349, 1987. In particular, a (G-NV) clone encoding the carboxy terminus of the G protein and overlapping into the neighboring NV gene of IHNV was used to confirm the sequence at the carboxy terminus of the glycoprotein gene. Suitable fragments were used to clone in both orientations into the polylinker sequences of the cloning vectors M13mp18 and M13mp19. The DNA sequence analysis was done by the dideoxynucleotide method of Sanger, et al., *Proc. Natl. Acad. Sci. USA,* 74:5463–5467, 1977. The entire sequence of the G8 insert was determined on both strands. In one series, fragments generated by the restriction endonucleases TaqI and PstI were subcloned into M13mp18 and M13mp19. In the other series, pG8 was digested with HindIII and random ends were generated with fast Bal31 nuclease (International Biotechnologies, Inc.) by digesting for various times (1–5 min.) under the conditions recommended by the manufacturer. The mixture was digested with BamHi, and the resulting Bal31 deletion fragments were cloned into the BamHi and SmaI sites of M13mp18. The nucleotide sequence data were analyzed for translational open reading frames, restriction endonuclease sites, and codon usage.

B. Sequencing Strategy

Clone pG8 was sequenced according to the strategy shown in FIG. 10. The DNA sequence of the viral insert in pG8 is shown in FIG. 11 in the messenger sense. The recombinant contains 1,609 residues excluding 17 As at the 3' end representing the oligo(dT)-primed cDNA construction. The accuracy of the sequence was ascertained by A-track sequence analysis of several of the smaller clones. The precise delineation of the 3' termini of the G gene was determined by sequence analysis of clones containing the intervening sequences between the G and NV genes.

C. Nucleotide Sequence of IHNV G Gene

There are two ATG start codons at positions 49 and 58 (coding for methionine as shown in FIG. 11 at amino acid positions 1 and 4, respectively) in the cDNA clone, both within a single open reading frame encoding a protein of 508 amino acids. The initial sequence of this single open reading frame from positions 46 to 61 is ACAATGGACACCATGA. Both ATG codons are preceded with A in the −3 position and the first ATG codon has a G at the +4 position after the start of the ATG codon. The optimal sequence for initiation by eucaryotic ribosomes has been determined by a survey of the 5' ends of eucaryotic mRNAs (Kozak, *Nucl. Acids Res.*, 9:5233–5252, 1981 and Kozak, *Nucl. Acids Res.*, 12:857–872, 1984) and defined by mutagenesis (Kozak, *Cell*, 44:283–292, 1986) to be ACCATGG. The purine in the −3 position occupies a dominant position for ribosome initiation and G in position +4 is also important. Thus, there is a "Kozak's box" at the first ATG start codon of the G gene open reading frame, and this suggests that the entire coding sequence for the G gene has been obtained.

The termination codon, TAA, at position 1573 occurs 34 nucleotides upstream of the poly(A) tail. A survey of the 50-base pair sequence preceding the polyadenylation site reveals no eucaryotic polyadenylation signal.

VI. Deduced Amino Acid Sequence of G Protein

The deduced protein of 56,795 daltons has an N-terminal hydrophobic signal peptide of 18 amino acids and a C-terminal hydrophobic anchorage domain of 27 amino acids (FIG. 11). There is a signal peptidase recognition sequence, Ala-X-Ser, at position 18, with the cleavage site located after residue 20. There are five possible N-glycosylation sites (Asn-X-Ser/Thr) in the gene at amino acid positions 56, 400, 401, 438, and 506. In all probability, only one of the residues at 400 or 401 in the sequence Asn-Asn-Thr-Thr is used, and the amino acid residue at 506 is probably not used because it lies within the cytoplasmic domain of the glycoprotein.

VII. Preparation of an IHNV Glycoprotein Subunit Vaccine

A subunit vaccine was prepared by the expression in *E. coli* of a viral G-protein epitope immunoreactive with IHNV neutralizing antisera, as described in Gilmore, et al., *Bio/Tech.*, 6:295–300, 1988. In particular, the viral epitope was expressed as a fusion protein with the trpE protein of *E. coli*.

A. Construction of Recombinant Plasmids

The construction of a recombinant plasmid containing the trpE promoter and gene fused to a fragment of the IHNV glycoprotein gene is shown in FIG. 9. Plasmid pG8 contains the entire coding sequences for the glycoprotein from IHNV isolated from Round Butte Hatchery, Oregon (Koener, et al., *J. Virol.*, 61:1342–1349, 1987. The 1.6 kb glycoprotein gene insert of pG8 was excised by cleavage with PstI and purified by gel electrophoresis in low-melting-temperature agarose (SeaKem, FMC Corporation Marine Colloids Div.). The purified fragment, digested with restriction endonuclease SaU.3AI, yielded 9 fragments ranging in size from 40 to 329 basepairs (bp). These fragments were ligated to the pATH3 trpE fusion protein expression vector (provided by T. J. Koerner and A. Tzagaloff of Columbia University) previously cleaved with BamHI in a T4 DNA ligase reaction (Mulcany, et al., *J. Fish Dis.*, 6:321–330, 1983). The entire mixture was used to transform *E. coli* strain MC1061 (Casadaban and Cohen, *J. Mol. Biol.*, 138:179–207, 1980) and transformants were identified by colony blot hybridization. Transformants were grown on Luria-Bertani (LB) agar plates containing 120 µg/mL ampicillin. The constructions were verified by DNA sequence analysis by the dideoxy method (Sanger, et al., *Proc. Natl. Acado Sci. USA*, 74:5463–5467, 1977.

Via the above method, recombinant plasmids containing fragments of the G gene were generated rather than plasmids containing the intact G gene.

B. Immunologic Detection of Viral Peptide Protein Expression

Transformants were analyzed for viral peptide production by immunologic detection. The transformant colonies were transferred to nitrocellulose by replica plating (Grunstein and Hogness, *Proc. Natl. Acad. Sci. USA*, 72:3961–3965, 1975) and the nitrocellulose was overlayed on minimal media M9 containing 1-percent casamino acids, 10 µg/mL indoleacrylic acid, and 120 µg/mL ampicillin (Mulcahy, et al., supra). The cells were allowed to grow overnight at 37° C. The cells were then lysed by exposure to chloroform vapor for 2 h and, subsequently, the filters were analyzed for viral antigen with rabbit anti-IHNV and horseradish peroxidase conjugated goat anti-rabbit immunoglobulin serum (Hsu, et al., *Appl. Env. Microbiol.*, 52:1353–1361, 1986).

Twelve colonies of transformants were selected. Plasmids were isolated from individual immunopositive colonies and digested with EcoRI and HindIII. An estimate of each insert's size was determined by agarose gel electrophoresis of the digested plasmid. The results indicated that there were only two different insert sizes, approximately 600 and 1800 bp, among the twelve colonies. The large size of these inserts suggested that two or more Sau3AI fragments were ligated together during the cloning procedure, as confirmed by DNA sequence analysis of the inserts. Plasmids p52G and p618G were selected as representatives of the groups with 600 bp and 1800 bp inserts, respectively.

E. coli DH5α, containing the transformed plasmid p618G, was deposited at the American Type Culture Collection on Jul. 27, 1988, the deposit having accession number ATCC 67752.

C. "Western" Immunoblotting

The insoluble E. coli lysates from positive cultures were prepared as described (Kleid, et al., Science, 214:1125–1129, 1981). Proteins were analyzed by sodium dodecyl sulfate polyacrylamide gel electrophoresis (SDS PAGE) on a 10-percent polyacrylamide gel by the discontinuous gel method (Laemmli, Nature, 227:680–685, 1970). The proteins distributed on the gel were electrophoretically transferred to 0.2 μm nitrocellulose (Towbin, et al., Proc. Natl. Acad. Sci. USA, 76:4350–4354, 1979). The Western blots were developed with rabbit anti-IHNV serum and rabbit antiserum prepared against purified IHNV glycoprotein.

p618G produced a trpE-fusion protein with an apparent molecular weight of 48000 Daltons. p52G produced a trpE-fusion protein with an apparent molecular weight of 49000 Daltons.

DNA sequence data for the plasmids showed that, in both p52G and p618G, the Sau3AI-329 bp fragment of the G gene was inserted in the correct reading frame with the E. coli structural gene for trpE. The 329 bp fragment encoded a peptide of approximately 11000 Daltons. Thus, for example, the trpE-G fusion protein of 49000 Daltons contained 37000 Daltons of the trpE polypeptide and the addition 11000-Dalton G protein fragment.

D. Immunization Trials in Fish

Bacterial crude lysates were prepared (Kleid, et al., supra) and used to immunize fish by immersion. A set of approximately 100 rainbow trout or chinook salmon (*Oncorhynchus tshawytscha*) fry were used for each control and immunized experimental group. The average weight of each fry at the time of immunization was 0.4 g.

Immunization by immersion was accomplished by bathing groups of 100 fry in 25 mL of the preparation (ca. 3 mg/mL total protein concentration) for i min. At that time, the immersion solution volume was increased to 250 mL with water and fish were incubated in this diluted solution for an additional 2 min. These fish were then placed in aquaria of 5 gallons with a water flow rate of 0.25 gal/min in a constant water temperature of 10° C. Approximately one month after immunization, each fish group was subdivided and challenged with varying doses of live, virulent IHNV. All dead fish were assayed for the presence of infectious IHNV in chinook salmon cells (CHSE-214) (Engelking and Leong, *Virol.,* 109:47–58, 1981). The data was analyzed statistically by estimation of logistic regression models.

The results indicated that fish immunized with trpE-G fusion protein were protected significantly against subsequent challenge with the Round Butte isolate of IHNV or with the more virulent Dworshak strain of IHNV. Mortality decreases of from 50 to 70 percent occurred in the immunized fish at the higher virus dilutions. Fish mock-immunized with a bacterial lysate containing the pATH3 vector with no viral insert showed mortality upon subsequent infection that was the same as in the nonimmunized control group.

VIII. Preparation of Vaccine

Subunit fish vaccines are thus prepared by growing and reproducing hybrid bacterial cells containing replicons that include an expressible viral gene coding for a desired viral protein, such as the IHNV glycoprotein or a portion thereof.

In most instances, vaccines according to the present invention are bacterins. The bacterial clone cells, having synthesized the desired viral protein, are killed, and lysed if necessary, by appropriate chemical agents such as strong acids or bases, detergents, formalin, chloroform and butanol. The resulting material, including the desired protein, is then suspended in a pharmaceutically acceptable diluent, usually water, to form the vaccine.

In the case of IHNV, a culture of the hybrid bacteria containing the desired viral replicon can be grown in nutrient broth until mid-log phase. The cells are then induced by the addition of indoleacrylic acid to a final concentration of 60 μg/mL and the culture is incubated for an additional 4 hours at 37° C. The bacteria were collected by centrifugation at 4,000×g and resuspended in TEN (50 mM Tris-HCl, pH 7.5; 0.5 mM EDTA; 0.3 M NaCl), treated on ice for 15 min with lysozyme (1 mg/mL), and made 0.2 percent in NP40. After 10 min, the sample was diluted with 120 mL of 1.5M NaCl and 12 mM $MgCl_2$ and stirred on ice with deoxyribonuclease (2 μg/mL, final concentration) for i hour as described by Kleid, et al., (*Science,* 214: 1124–1129, 1981). Another method that has also been used successfully to break open the cells is to resuspend the bacteria in one-tenth volume TE (0.02M Tris-HCl, pH 7.5; 0.001 M EDTA) and then subjecting the suspension to 15,000 psi in a Carver French Press for 5 min. The lysates from both methods can be stored at −70° C. with no loss of activity.

IX. Methods of Immunization of Fish

There are a number of methods by which fish can be vaccinated. Vaccines formed by the above-described procedure can be administered orally or by immersion, spraying or injection. For efficiency, injection is least preferred, especially if an acceptable level of immunity can be obtained by another route.

The most efficient vaccination route and dosage are determined by multiple immunization of fish of a species that is particularly susceptible to the viral disease of interest and determining the resistance of such fish to a live virus challenge. Sockeye salmon fry (*Oncorhynchus nerka*) are very susceptible to IHN disease and thus are good subjects on which to test the effectiveness of an IHNV vaccine.

If an otherwise desirable vaccine is found to be effective for an insufficient length of time, a booster dose can be given to complete the development of protective immunity.

Tests can be conducted to establish the developmental stage at which fish receive the greatest benefit from vaccine exposure. The vaccination of fish for IHNV anti-viral immunity must be done at a time when this protection is most needed. Since IHN disease may occur in fish at the yolk-sac fry stage, it is important to determine whether immunization will occur if eggs or yolk-sac fry are exposed to the vaccine. Groberg reported that two of six fish exposed to a *Vibrio anguillarum* bacterin as embryonated eggs exhibited serum agglutination immunity to *V. anguillarum* (Groberg, Ph.D. thesis, Oregon State University, 1982).

Thus, to determine the optimum time of exposure, it is best to compare vaccination of eggs at water hardening, yolk-sac fry, fry, fingerlings, and yearlings. For IHNV, *O. nerka* eggs can be immunized by hardening in an aqueous solution containing the IHNV glycoprotein, 50–100 μg/mL. Yolk-sac fry are immunized by immersion in an aqueous solution of IHNV glycoprotein (50–100 μg/mL) for five minutes. Fry (0–14 days old after start of feeding) are immunized in the same manner, Immunization of fingerlings (15–269 days old after start of feeding) is accomplished by immersion in an aqueous solution of IHNV glycoprotein (50–100 μg/mL protein) for five minutes. Yearling fish (270+ days after start of feeding) are immunized by immersion in an aqueous solution of IHNV glycoprotein (50–100 μg/mL protein) for five minutes.

While I have shown and described preferred embodiments of my invention, it will be apparent to those skilled in the art that changes may be made without departing from my invention in its broader aspects. The appended claims are therefore to cover all such changes and modifications as follow in the true spirit and scope of my invention.

I claim:

1. A process for immunizing fish against infection by the Infectious Hematopoietic Necrosis (IHN) virus, the method comprising vaccinating fish with a vaccine which induces an immune response in fish, wherein the vaccine includes an antigen from a portion of the G protein encoded by a 329 base-pair fragment produced by digesting a glycoprotein gene of IHNV with Sau-3AI, the antigen having been expressed by a replicon with joined DNA which encodes the antigen.

2. A vaccine which induces an immune response in fish against infection by the Infectious Hematopoietic Necrosis Virus (IHNV), the vaccine comprising an antigen from a portion of the G protein encoded by a 329 base-pair fragment produced by digesting a glycoprotein gene of IHNV with Sau3AI, the antigen having been expressed by a replicon with joined DNA that encodes for the antigen.

3. A vaccine of claim 2 wherein the antigen comprises ail of the G protein.

4. A polypeptide encoded by a 329 base-pair fragment of a DNA sequence as shown in FIG. 11, the 329 base-pair fragment being produced by digesting a glycoprotein gene of IHNV with Sau3AI, the polypeptide inducing an immune response against IHNV infection in susceptible fish.

5. The process according to claim 1 wherein the 329 base-pair fragment includes base pairs 1053–1382 as shown in FIG. 11.

6. The vaccine according to claim 2 wherein the 329 base-pair fragment includes base pairs 1053–1382 as shown in FIG. 11.

* * * * *